United States Patent [19]

Kristiansen et al.

[11] Patent Number: 5,107,856
[45] Date of Patent: Apr. 28, 1992

[54] MULTIPLE LEAD SUTURE SLEEVE

[75] Inventors: Jeffrey C. Kristiansen, Simi Valley; Ronald V. Forino, St. Helena; Paul E. Kreyenhagen, Castaic, all of Calif.

[73] Assignee: Siemens-Pacesetter, Inc., Sylmar, Calif.

[21] Appl. No.: 639,643

[22] Filed: Jan. 10, 1991

[51] Int. Cl.⁵ .............................................. A61N 1/00
[52] U.S. Cl. .................................... 128/785; 604/175; 128/DIG. 26; 128/419 P
[58] Field of Search ................ 606/139; 604/174–175, 604/178–180; 128/784–786, 419 P, DIG. 26

[56] References Cited

U.S. PATENT DOCUMENTS

| | | | |
|---|---|---|---|
| 4,276,882 | 7/1981 | Dickhudt et al. | 128/419 P |
| 4,516,584 | 5/1985 | Garcia | 128/785 |
| 4,553,961 | 11/1985 | Pohndorf et al. | 604/175 |
| 4,650,473 | 3/1987 | Bartholomew et al. | 128/DIG. 26 |
| 4,672,979 | 6/1987 | Pohndorf | 128/784 |
| 4,906,233 | 3/1990 | Moriuchi et al. | 604/174 |
| 4,944,088 | 7/1990 | Doan et al. | 128/642 |

FOREIGN PATENT DOCUMENTS 1308572 12/1989 Jordan ........................ 128/DIG. 26

Primary Examiner—C. Fred Rosenbaum
Assistant Examiner—Ron Stright, Jr.
Attorney, Agent, or Firm—Malcolm J. Romano; Lisa P. Weinberg

[57] ABSTRACT

A suture sleeve for securing the leads of a multiple lead implantable medical device includes lead gripping and anchoring portions. The sleeve has a pair of flexible side walls and longitudinally extending channels for receiving the leads. The side walls of at least the gripping portion have longitudinally extending, confronting, spaced apart edges and comprises two layers one of which is formed of a soft plastic such as silicone and the other of which is formed of a harder but flexible material such as polysulfone. Sutures placed and tied about the gripping portion compress the sleeve about the leads. Tightening of the sutures brings the confronting edges of the gripping portion of the sleeve into engagement thereby precluding further compression of the sleeve and preventing damage to the leads.

16 Claims, 5 Drawing Sheets

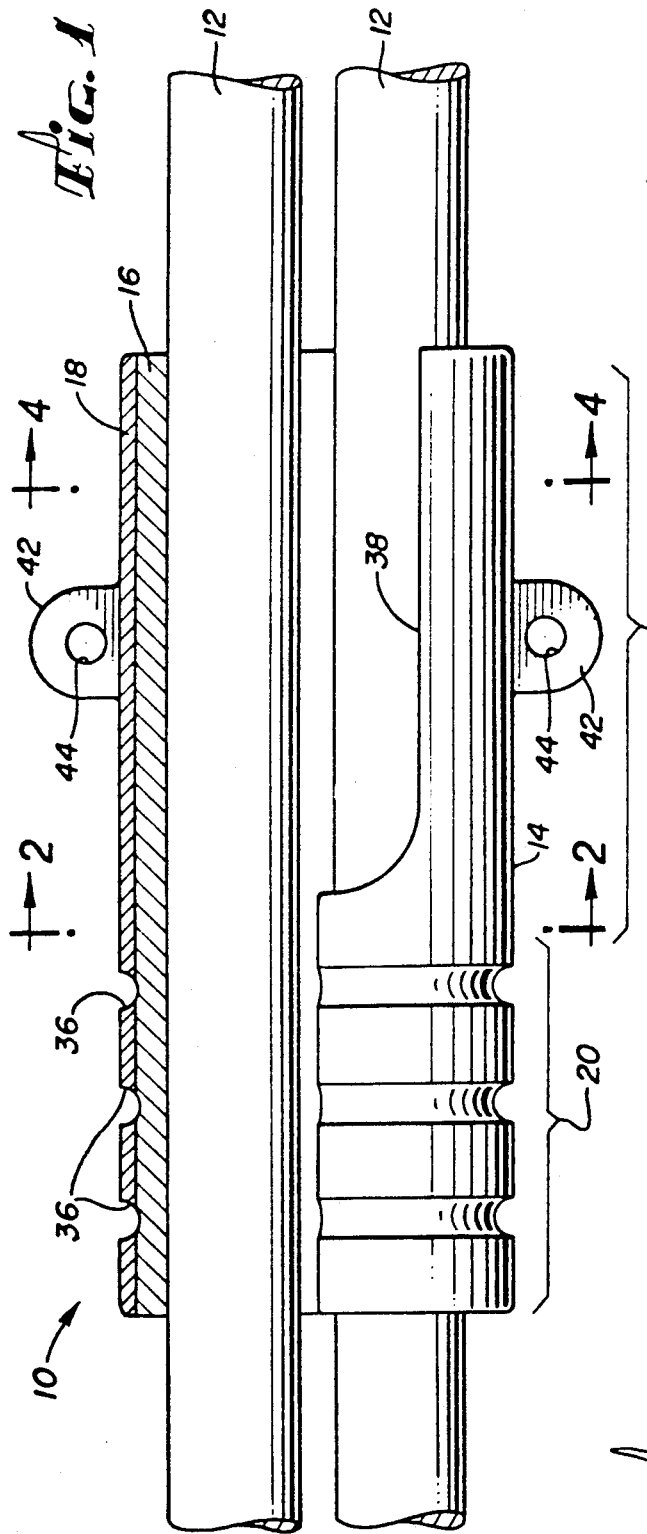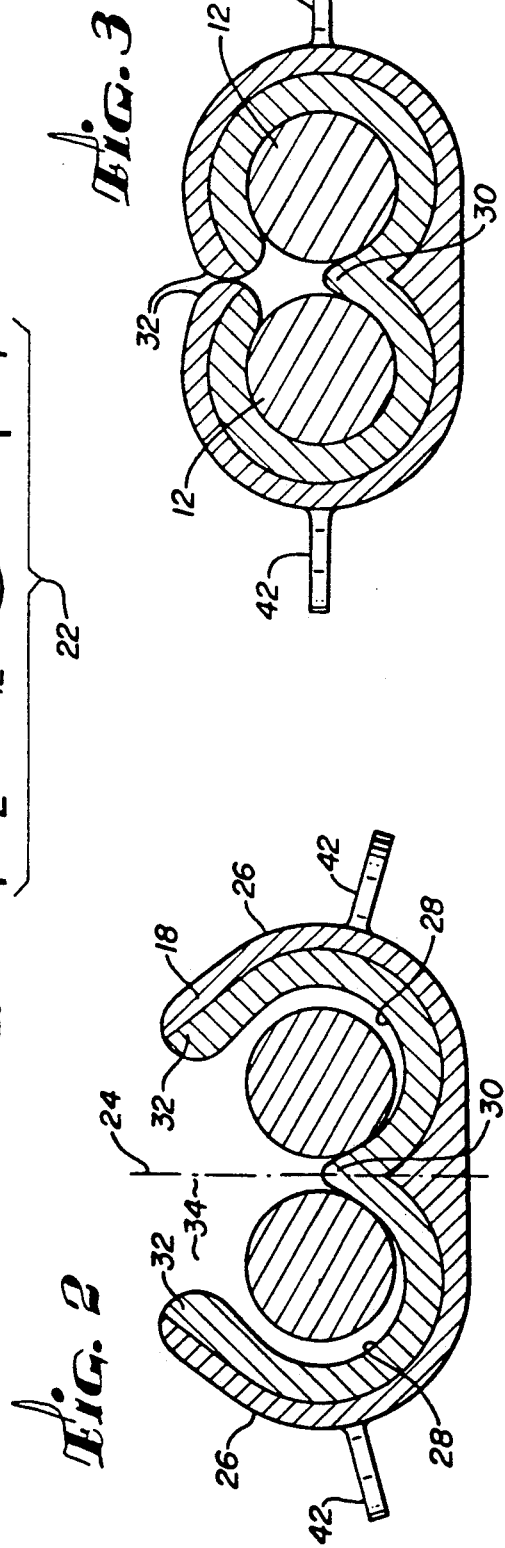

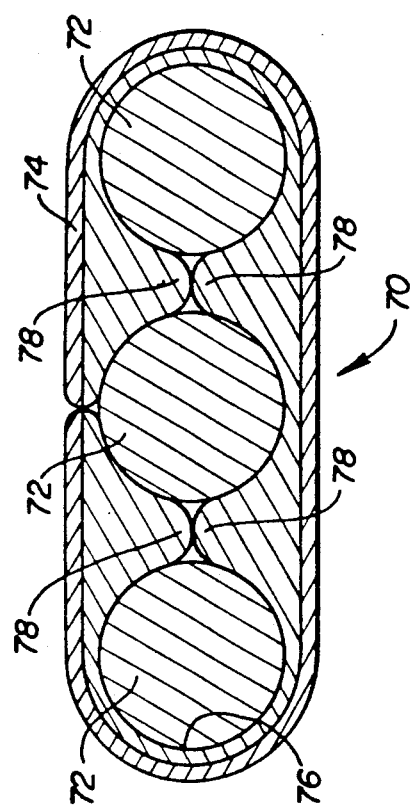
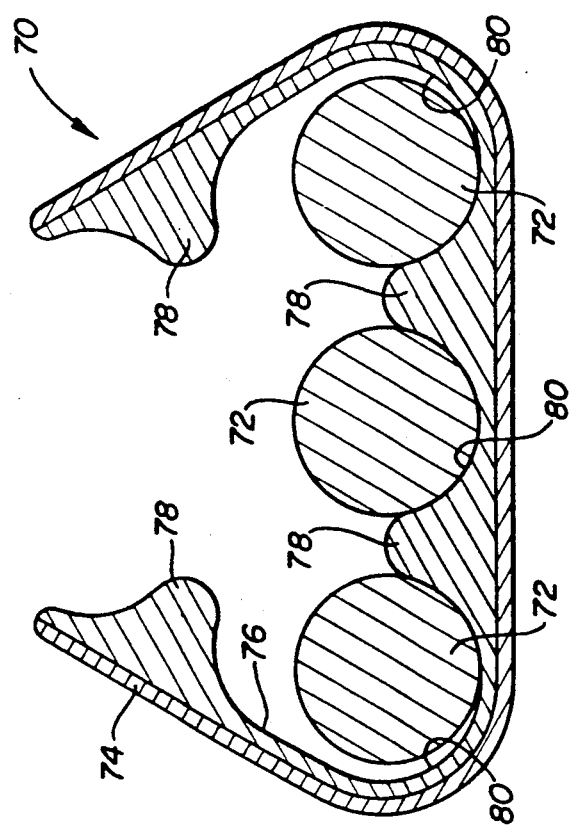

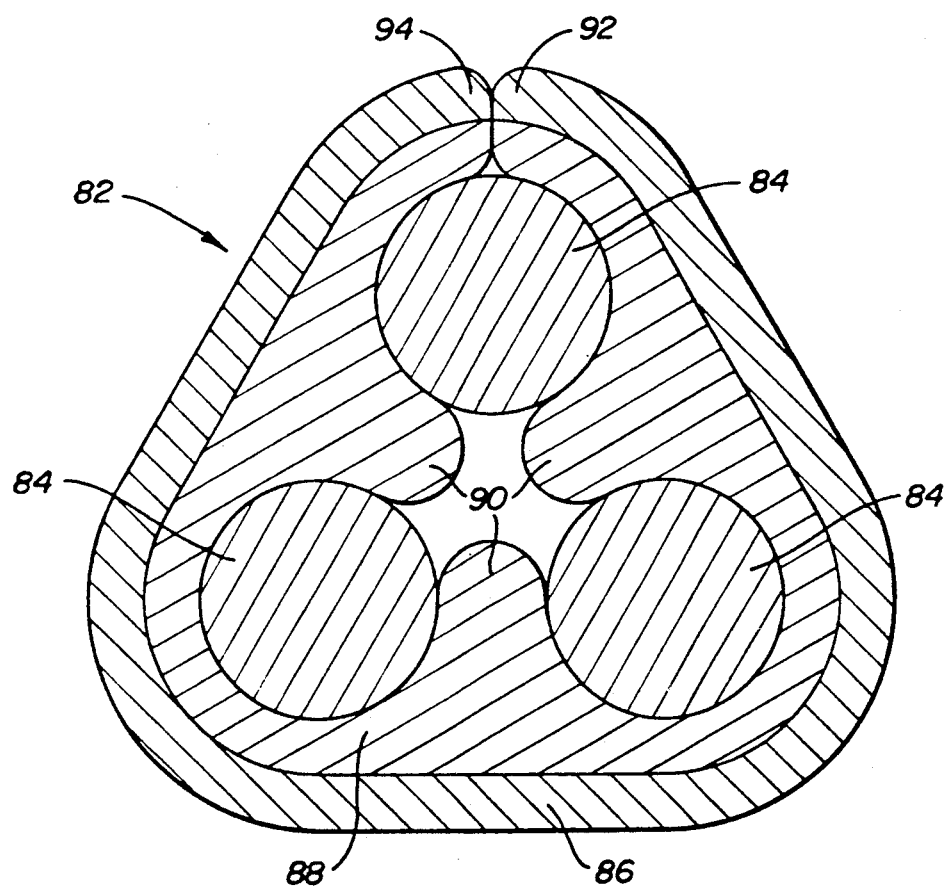

MULTIPLE LEAD SUTURE SLEEVE

FIELD OF THE INVENTION

This invention relates generally to suture sleeves for anchoring the leads of implantable medical devices, and more particularly, to a suture sleeve for securely gripping the leads of a multiple lead pacemaker while preventing damage to the leads.

BACKGROUND OF THE INVENTION

During the implantation of an endocardial lead, the lead is introduced into the heart using a venous approach, usually from the subclavian or cephalic vein in the shoulder area under the pectoral muscle. To keep the lead from shifting in the vein, the lead is secured to both the vein and to the underlying muscle tissue. A suture placed around the vein near the lead entry point ties the lead to the vein, and a suture sleeve around the lead is used to anchor the lead to adjacent tissue.

Suture sleeves in present use are generally tubular structures molded out of a soft, implantable elastomer such as silicone. After the lead is tied to the vein, the sleeve is slid along the lead to the location at which the lead is to be anchored to the underlying tissue. One or more sutures are then tied around the sleeve to compress it and thereby anchor it to the lead. Circumferential grooves in the outer surface of the sleeve are typically provided for this purpose. The last step is to anchor the sleeve to the body tissue; such anchoring is typically furnished by sutures passed through eyelets formed in a pair of tabs projecting from the sleeve.

Existing sleeves have several drawbacks. For example, only one lead can be secured within each suture sleeve. However, because many implants now use dual chamber pacemakers requiring at least two leads, this means that two or more sleeves must be secured to the surrounding tissue.

In addition, because most present suture sleeves are closed tubular structures that must be slid along the lead into position, sufficient flexibility must be provided to facilitate sliding the sleeve around curves in the lead. Furthermore, it is difficult for the physician to control the degree to which present sleeves are compressed when they are secured to a lead. The ligature around the sleeve must be tight enough to prevent the lead from sliding in the anchoring sleeve but not so tight as to damage the insulation of the lead. This is especially important with bipolar coaxial leads because an excessively tight ligature could rupture the lead insulation and cause the outer and inner electrical leads to come into contact with each other resulting in a short circuit.

Accordingly, it is an object of the present invention to provide a single suture sleeve for securely gripping and anchoring the leads of a multiple lead pacemaker.

It is another object of the present invention to permit positioning of the sleeve on the leads without having to slide it along the length of the leads.

It is a further object of the invention to provide a lead gripping and anchoring suture sleeve in which the compression of the sleeve is self-limiting so as to prevent lead damage.

SUMMARY OF THE INVENTION

In accordance with one specific exemplary embodiment of the invention, there is provided a multiple lead, elastomeric suture sleeve defining parallel, transversely spaced apart, longitudinally extending channels for receiving the leads. The sleeve includes a pair of flexible side walls having confronting, spaced apart edges defining a longitudinally extending opening through which the leads may be inserted. Preferably, the sleeve is constructed of two layers, one of which is a soft elastomer such as silicone and the other of which is a harder but flexible material such as polysulfone.

Further in accordance with this specific embodiment, the exterior surface of the sleeve includes a plurality of suture receiving grooves. Sutures placed and tied in the grooves compress the sleeve into gripping relationship with the leads and bring the edges of the side walls into engagement thereby preventing further compression of the sleeve.

The suture sleeve also includes an anchoring portion having projecting tabs with eyelets for receiving sutures for attaching the sleeve to adjacent tissue.

By limiting compression of the sleeve, damage to the leads is prevented. Furthermore, the split construction of the sleeve allows it to be placed on the leads at the point at which the leads are to be anchored thereby eliminating the need to slide the sleeve along the leads. Accordingly, the length of the stiffer layer need not be unduly limited, nor does it need to be segmented for added flexibility.

BRIEF DESCRIPTION OF THE DRAWINGS

Further objects, advantages and features of the invention will become apparent from the detailed description of the preferred embodiments, below, when read in conjunction with accompanying drawings, in which:

FIG. 1 is a top plan view, partly in cross section, of a multiple lead suture sleeve in accordance with a first embodiment of the invention employing dual leads, with the sleeve shown in its closed, lead-gripping configuration;

FIG. 2 is a transverse sectional view of the sleeve of FIG. 1 in its open configuration, as seen along the lines 2—2;

FIG. 3 is a transverse sectional view of the sleeve of FIG. 1 in its closed configuration, as also seen along the lines of 2—2;

FIGS. 8 and 9 are transverse sectional views of a multiple lead suture sleeve in accordance with a fourth embodiment of the invention employing three leads; and FIG. 10 is a transverse sectional view of a fifth embodiment of the invention.

DETAILED DESCRIPTION OF THE PREFERRED EMBODIMENTS

Figure 4:
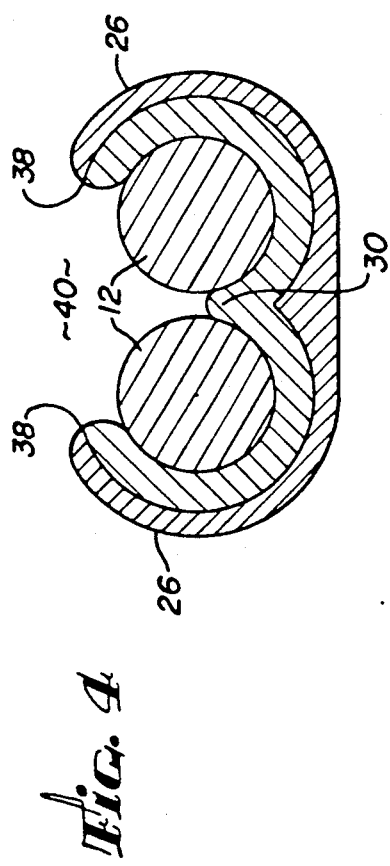
FIG. 4 is a transverse sectional view of the sleeve of FIG. 1 as seen along line 4—4.

With reference to FIGS. 1-4 of the drawings, there is shown a first embodiment of the invention comprising a multiple lead suture sleeve 10 adapted to grip and anchor the leads 12 of a dual or plural lead implantable pacemaker. Although an implantable pacemaker is described in combination with plural leads, it is to be understood that other implantable medical devices are also contemplated by the invention. For example, the invention may be used with, but not limited to, defibrillators and cardioverters. Because the structure of such leads is well known in the art, the details thereof have been omitted from the drawings for the sake of simplicity.

The sleeve 10 is in the form of a unitary, elongated body 14 including an inner layer 16 and an outer layer 18 formed and bonded together using techniques well known in the art. The inner layer 16 is made of a soft implantable elastomer, such as silicone or polyurethane, while the outer layer 18 is made of relatively hard but flexible implantable plastic such as polysulfone or delrin. Alternatively, the outer layer 18 may be fabricated of an implantable metal or metallic alloy such as titanium, platinum, platinum-iridium or stainless steel.

The sleeve of FIGS. 1–4 has two portions: a lead gripping portion 20 and an anchoring portion 22. In the open configuration of the sleeve (as shown in FIG. 2), the lead gripping portion 20 has a generally double C-shaped cross section that is symmetrical about a central, vertical plane 24. More specifically, the gripping portion 20 has a pair of inwardly directed, curved side walls 26 each blending into an arcuate channel 28 for receiving one of the leads 12. The channels 28 are joined by an inwardly projecting lead divider 30 whose inner walls form part of the channels 28. The side walls 26 of the gripping portion 20 have confronting, spaced apart edges 32 defining a longitudinal opening 34 through which the leads 12 are inserted after they have been positioned in the heart. The exterior of the gripping portion 20 has a plurality of parallel, suture-receiving grooves 36 that extend circumferentially about the gripping portion. Three such grooves are shown by way of example.

The anchoring portion 22 of the sleeve is an extension of the gripping portion and generally has the same cross-sectional configuration. The upper edges 38 of the anchoring portion, however, are not extensions of the edges 32; they are set back so that with the edges 32 in engagement, as shown in FIGS. 1 and 3, a longitudinally extending clearance opening 40 (see FIGS. 1 and 4) remains between the edges 38. This assures that the edges 38 will not interfere with closure of the gripping portion 20.

A pair of projecting tabs 42, formed integrally with the sleeve, have eyelets 44 adapted to receive sutures (not shown) for tying the sleeve to the surrounding tissue.

In use, after the dual leads 12 have been introduced into the heart and measurements made to verify attainment of mechanically and anatomically stable positions, the leads are anchored to the underlying muscle tissue. The portions of the leads adjacent the venous entry are inserted into the sleeve 10 through the longitudinal opening 34 and seated within the channels 28. Sutures (not shown) are placed about the grooves 36 in the gripping portion 20 of the sleeve and tightened so as to bring the confronting edges 32 into engagement. The hard outer layer 18 prevents further closure of the sleeve thereby limiting compression of the leads 12. With the sleeve 10 closed, the sutures in the grooves 36 are then tied in a knot. In FIG. 3, the sleeve of FIG. 1 is shown in cross section also along the lines of 2—2 with the sleeve in the closed configuration. As shown in FIG. 3, the divider 30 serves to maintain separation between the leads 12 after the sleeve has been closed by the suture ties.

The sleeve 10 is so dimensioned that in the closed configuration shown in FIGS. 1 and 3 the sleeve has been compressed sufficiently to secure the leads against movement relative to the sleeve but not enough to damage the leads.

Finally, the sleeve is anchored to the adjacent tissue utilizing sutures passed through the eyelets 44.

Figure 5:
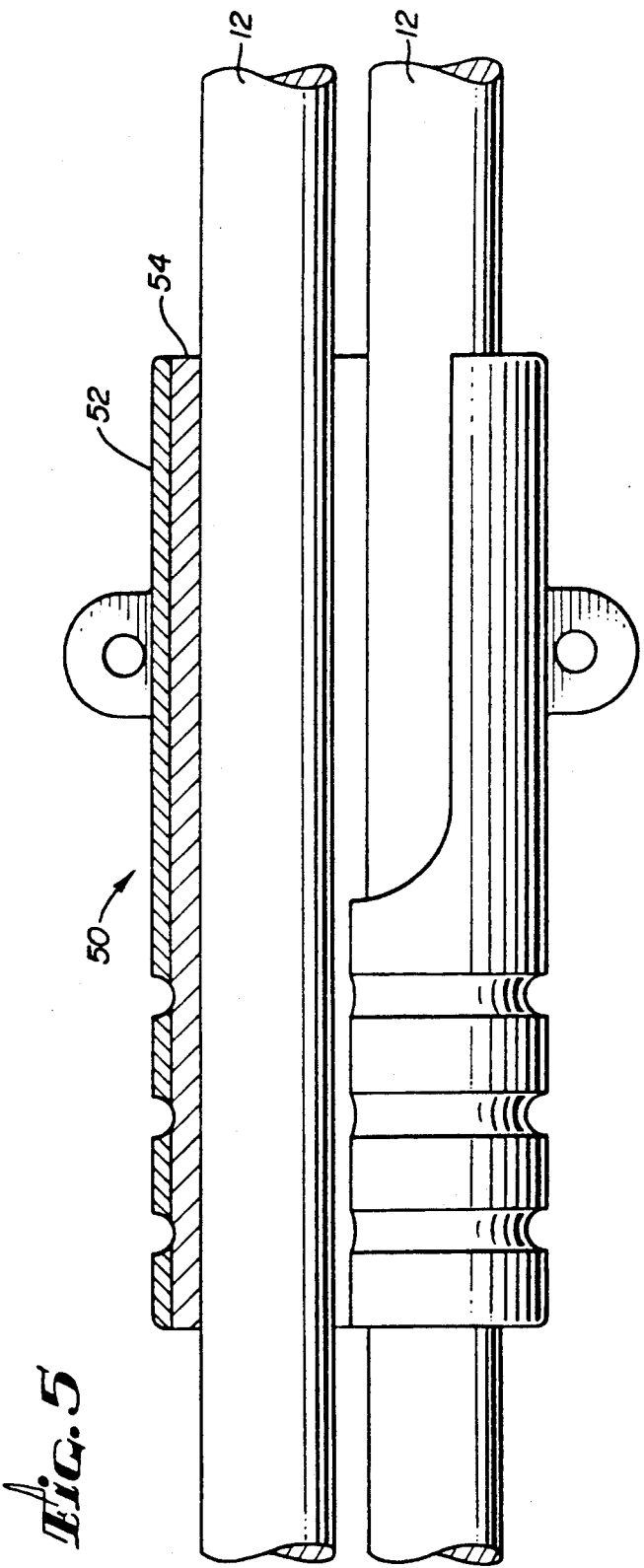
FIG. 5 is a top, plan view, partly in cross section, of a dual lead suture sleeve in accordance with a second embodiment of the invention, with the sleeve shown in its closed configuration.

FIG. 5 shows an alternative embodiment of the invention comprising a suture sleeve 50 structurally and operationally identical to the sleeve 10 of FIGS. 1–4 except that the materials from which the sleeve 50 is fabricated are reversed. Thus, the sleeve 50 has an outer layer 52 made of a soft plastic and an inner layer 54 formed of stiffer material as already described.

Figure 6:
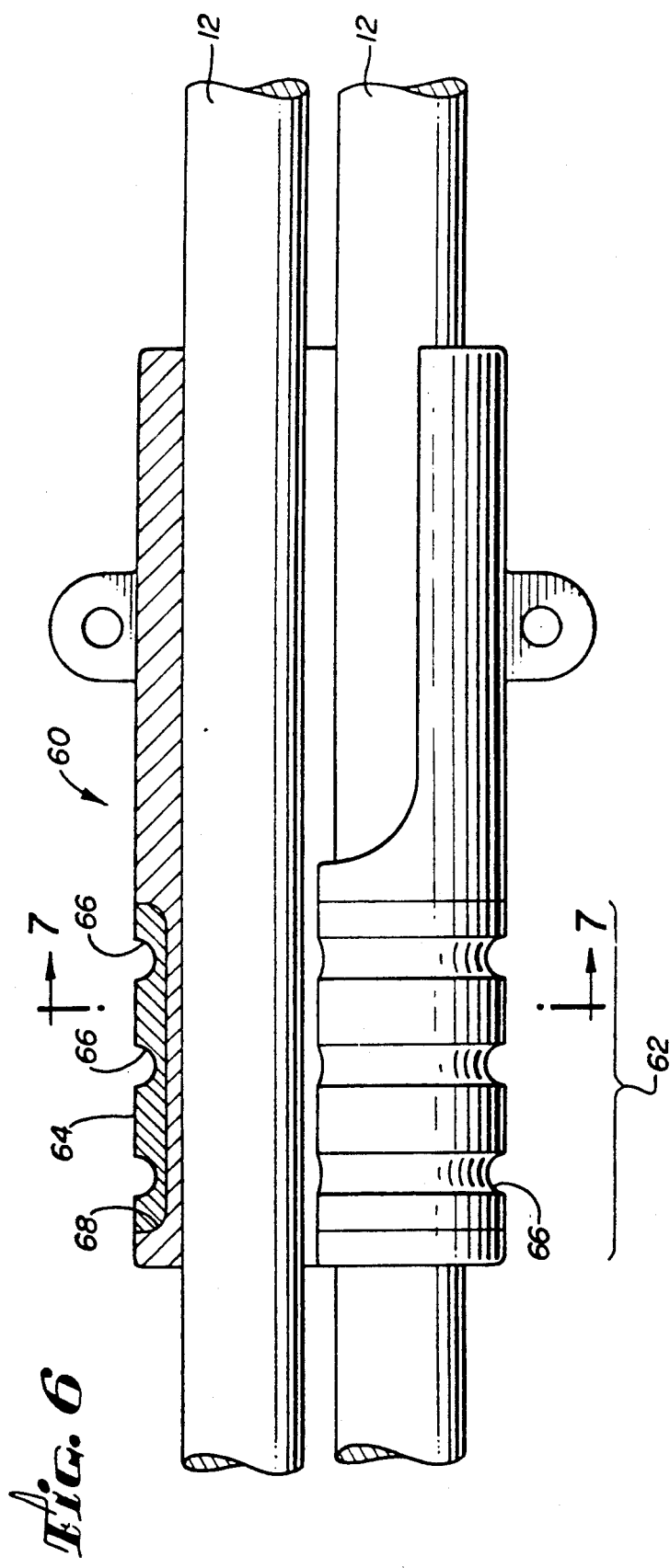
FIG. 6 is a top, plan view, partly in cross section, of a dual lead suture sleeve in accordance with a third embodiment of the invention, with the sleeve shown closed.
Figure 7:
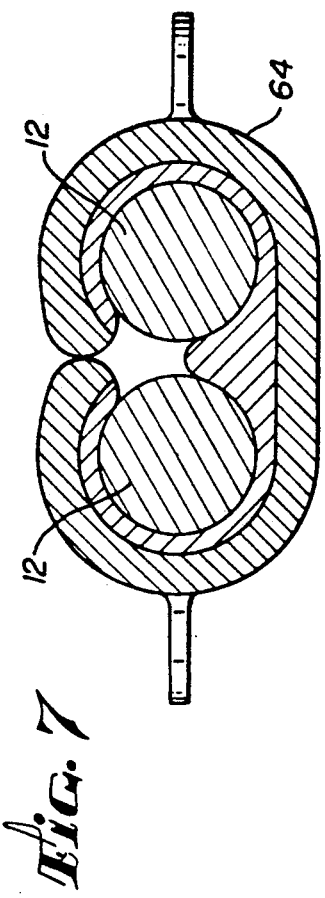
FIG. 7 is a transverse sectional view of the sleeve of FIG. 6 as seen along the line 7—7.

FIGS. 6 and 7 depict a third, dual lead embodiment comprising a suture sleeve 60 made principally of soft plastic such as silicone, for example. Encircling the lead gripping portion 62 of the sleeve 60 is an insert 64 of harder but flexible material of the kind previously described and including a series of suture receiving grooves 66. The gripping portion of the sleeve 60 is preferably recessed at 68 for receiving the insert 64. In all other respects, the configuration of the sleeve 60 and its cooperation with the leads 12 are the same as the earlier described embodiments.

FIGS. 8 and 9 depict a fourth embodiment in which a suture sleeve 70 similar to those previously described can accommodate three lead bodies 72. FIGS. 8 and 9 show in cross section the gripping portion of the sleeve 70 which comprises an outer hard plastic layer 74 and an inner soft plastic layer 76. The inner layer includes inwardly projecting top and bottom dividers 78 which, in the closed configuration of the sleeve (shown in FIG. 9), are interposed between the lead bodies 72 so as to maintain separation between them. A longitudinal channel 80 is formed in the soft plastic inner layer for receiving each lead body 72.

With the leads 72 inserted in the channels 80, the sleeve is closed (as shown in FIG. 9) and, in the manner already described, tied with sutures disposed in grooves (not shown) formed in the outer surface of the gripping portion of the sleeve 70.

FIG. 10 depicts a fifth embodiment in which a suture sleeve 82, similar to those previously described, can accommodate three lead bodies 84. As is apparent from the cross section of FIG. 10, the overall outer peripheral surface of outer layer 86 is in the general shape of a triangle. Outer layer 86 preferably comprises a hard plastic, whereas inner layer 88 preferably comprises a soft plastic.

The inner layer 88 includes a series of inwardly projecting lobes or dividers 90 which when the suture sleeve is in the closed position, as shown in FIG. 10, cradle lead bodies 84 into a fixed spaced-apart relationship relative to each other. Although not shown but in a manner similar to that previously described, when sutures are tied in grooves (not shown) formed in the outer surface of the suture sleeve end points 92 and 94 come together in contact forcing the lead bodies 84 in gripping relationship within the suture sleeve between dividers 90. By virtue of the mutual contact of end points 92 and 94, further compression of the suture sleeve under the action of the tightened sutures, is opposed, thereby preventing any further compression of the lead bodies 84.

The embodiment of FIG. 10, in addition to those already described, should be considered only one of many other possible configurations contemplated by the invention. A square cross section, for example, may under some conditions also be selected as the suture sleeve of choice when considering specific applications.

It will be obvious to those skilled in the art that the sleeve 70 may be modified to accommodate four or more lead bodies, and that the lead bodies may be of different sizes. For example, a lead of one size can be used in the atrium for sensing and pacing, a different size lead can be used in the ventricle for sensing and pacing, and a third lead can be used for a rate responsive system sensor. Other leads that may be used include a defibrillator sensor lead and a defibrillator patch lead. While various modifications and alternative constructions of the invention will be obvious to those skilled in the art, only specific, preferred embodiments thereof have been shown in the drawings and described in detail. It should be understood, however, that there is no intention to limit the invention to the specific forms or examples illustrated and described. On the contrary, the intention is to cover all modifications, alternative constructions and equivalents falling within the spirit and scope of the invention as defined by the appended claims.

What is claimed is:

1. A suture sleeve for anchoring the leads adapted to be used with an implantable medical device, the sleeve including flexible side walls and transversely spaced apart, longitudinally extending lead receiving channels, at least a portion of the length of said walls having confronting, spaced apart edges defining a longitudinally extending opening, the exterior surface of said portion of said wall having at least one groove extending about the outer surface in a generally transverse plane, the sleeve being adapted to receive the leads through the longitudinal opening defined by the spaced apart edges of the side walls, whereby a suture placed and tied in each of said at least one groove compresses said sleeve about said leads in gripping relationship therewith, thereby bringing said confronting edges into engagement thereby preventing further compression of said sleeve to prevent damage to the leads.

2. A suture sleeve, as defined in claim 1, in which adjacent lead receiving channels are joined by an inwardly projecting divider, the divider maintaining separation between the adjacent leads after said confronting edges have been brought into engagement.

3. A suture sleeve, as defined in claim 1, in which said portion of the length of said side walls define a gripping portion of the sleeve, the sleeve including an anchoring portion extending from the gripping portion and having means for attaching the sleeve to adjacent tissue.

4. A suture sleeve, as defined in claim 3, in which the anchoring portion has side walls having spaced apart edges which do not come into engagement upon compression of the sleeve about the leads.

5. A suture sleeve, as defined in claim 1, said sleeve formed of an elastomeric material and in which the side walls of the sleeve comprise two layers, one of the layers being soft plastic, the other layer being of hard but flexible plastic.

6. A suture sleeve for securing the leads of a dual lead implantable medical device, the sleeve having a generally double C-shaped cross section including a pair of curved side walls and a pair of transversely spaced apart, lead receiving arcuate channels, a portion of the length of said walls having confronting, spaced apart edges defining a longitudinally extending opening, the exterior surface of said portion having a plurality of grooves, each groove extending about the outer surface in a generally transverse plane, the sleeve being adapted to receive the leads through the longitudinal opening defined by the edges of the side walls, whereby sutures placed and tied in said grooves compress said sleeve about said leads in gripping relationship therewith, thereby bringing said confronting edges into engagement thereby preventing further compression of said sleeve to prevent damage to the leads.

7. A suture sleeve, as defined in claim 6, in which the lead receiving channels are joined by an inwardly projecting divider, the divider maintaining separation between the leads after said confronting edges have been brought into engagement.

8. A suture sleeve, as defined in claim 6, in which said portion of the length of said side walls define a gripping portion of the sleeve, the sleeve including an anchoring portion extending from the gripping portion and having means for attaching the sleeve to adjacent tissue.

9. A suture sleeve, as defined in claim 8, in which the anchoring portion has side walls having spaced apart edges which do not come into engagement upon compression of the sleeve about the leads.

10. A suture sleeve, as defined in claim 6, said sleeve formed of an elastomeric material and in which the side walls of the sleeve comprise two layers, one of the layers being soft plastic, the other layer being of hard but flexible plastic.

11. An elongated suture sleeve for securing the lead means of a cardiac pacemaker, the lead means comprising at least two leads, the sleeve including a longitudinally extending channel for receiving each lead, the channels being spaced apart transvenously, the sleeve having a side wall with an interior surface for gripping the lead means and suture receiving means extending about the sleeve, at least the portion of the length of the sleeve having the suture receiving means comprising two layers, one of the layers being of flexible material harder than the material of the other layer and having confronting, spaced apart edges, said confronting edges being so spaced as to be brought into engagement in response to placement and tying of suture means in said suture receiving means to thereby limit compression of the sleeve to prevent damage to the lead means.

12. A suture sleeve, as defined in claim 11, which includes an anchoring portion extending from said first mentioned portion, the anchoring portion including means for attaching the sleeve to adjacent tissue.

13. A suture sleeve, as defined in claim 12, in which both layers extend the entire length of the sleeve.

14. A suture sleeve, as defined in claim 12, in which the anchoring portion includes a side wall having longitudinally extending, spaced apart edges that do not come into engagement upon tying of said suture means.

15. An elastomeric suture sleeve for securing the leads of a multiple lead implantable medical device, the sleeve defining longitudinally extending lead receiving channels, the exterior surface of said wall having at least one groove extending about the outer surface in a generally transverse plane, whereby a suture placed and tied in said at least one groove compresses said sleeve about said leads in gripping relationship therewith, said sleeve including means for anchoring the sleeve to surrounding tissue.

16. A suture sleeve, as defined in claims 1, 6 or 15, in which said implantable medical device comprises a pacemaker.

* * * * *